(12) United States Patent
Yoshimoto et al.

(10) Patent No.: US 11,498,895 B2
(45) Date of Patent: Nov. 15, 2022

(54) PROCESS AND APPARATUS FOR UREA PRODUCTION

(71) Applicant: TOYO ENGINEERING CORPORATION, Tokyo (JP)

(72) Inventors: Kenji Yoshimoto, Narashino (JP); Keigo Sasaki, Narashino (JP)

(73) Assignee: TOYO ENGINEERING CORPORATION, Tokyo (JP)

(*) Notice: Subject to any disclaimer, the term of this patent is extended or adjusted under 35 U.S.C. 154(b) by 0 days.

(21) Appl. No.: 17/260,834

(22) PCT Filed: Jul. 2, 2019

(86) PCT No.: PCT/JP2019/026340
§ 371 (c)(1),
(2) Date: Jan. 15, 2021

(87) PCT Pub. No.: WO2020/021998
PCT Pub. Date: Jan. 30, 2020

(65) Prior Publication Data
US 2021/0230104 A1 Jul. 29, 2021

(30) Foreign Application Priority Data

Jul. 26, 2018 (JP) .............................. JP2018-140072

(51) Int. Cl.
*C07C 273/04* (2006.01)
*B01J 3/04* (2006.01)
(Continued)

(52) U.S. Cl.
CPC .............. *C07C 273/04* (2013.01); *B01J 3/04* (2013.01); *B01J 19/0013* (2013.01); *C07C 275/02* (2013.01)

(58) Field of Classification Search
None
See application file for complete search history.

(56) References Cited

U.S. PATENT DOCUMENTS

| 4,053,507 | A | | 10/1977 | Inoue et al. |
| 4,314,077 | A | * | 2/1982 | Zardi ................ C02F 11/08 564/72 |
| 5,936,122 | A | * | 8/1999 | Kojima ............. C07C 273/04 564/72 |

FOREIGN PATENT DOCUMENTS

| EP | 1 728 783 A1 | 12/2006 |
| EP | 1 876 171 A1 | 1/2008 |

(Continued)

OTHER PUBLICATIONS

Office Action issued in Bangladesh Patent Application No. 174/2019/2701, dated Oct. 22, 2020.
(Continued)

*Primary Examiner* — Amy C Bonaparte
(74) *Attorney, Agent, or Firm* — Foley & Lardner LLP

(57) ABSTRACT

There is provided a process and an apparatus for urea production in which preheating of raw material ammonia or heating in a medium-pressure decomposition step can be performed at a relatively low pressure while preventing decrease in an overall heat transfer coefficient. A process for urea production includes: a synthesis step of generating a urea synthesis solution; a high-pressure decomposition step of heating the urea synthesis solution to separate a gaseous mixture containing ammonia and carbon dioxide from the urea synthesis solution; a condensation step of condensing the gaseous mixture; a medium-low-pressure steam generation step of reducing a pressure of medium-pressure steam condensate obtained in the high-pressure decomposition step to a medium-low pressure to generate medium-low-pressure steam and medium-low-pressure steam condensate; and one or both of a medium-pressure decomposition step and an ammonia preheating step.

18 Claims, 2 Drawing Sheets

(51) Int. Cl.
*B01J 19/00* (2006.01)
*C07C 275/02* (2006.01)

(56) References Cited

FOREIGN PATENT DOCUMENTS

| | | |
|---|---|---|
| GB | 1 542 371 | 3/1979 |
| GB | 2557080 A | 6/2018 |
| JP | 52-068129 | 6/1977 |
| JP | 61-010547 | 1/1986 |
| JP | 10-182587 A | 7/1998 |
| WO | WO 03/064379 A1 | 8/2003 |
| WO | WO 2017/043390 A1 | 3/2017 |
| WO | WO 2017/043391 A1 | 3/2017 |

OTHER PUBLICATIONS

International Search Report issued in International Patent Application No. PCT/JP2019/026340, dated Oct. 8, 2019.
Supplemental European Search Report issued in co-pending European Patent Application No. 19840077, dated Apr. 19, 2022.

\* cited by examiner

PROCESS AND APPARATUS FOR UREA PRODUCTION

CROSS-REFERENCE TO RELATED APPLICATIONS

This application is the U.S. National Stage of International Patent Application No. PCT/JP2019/026340, filed Jul. 2, 2019, which claims priority to Japanese Patent Application No. 2018-140072, dated Jul. 26, 2018. The contents of these applications are incorporated herein by reference in their entirety.

TECHNICAL FIELD

The present invention relates to a process and an apparatus for producing urea from ammonia and carbon dioxide.

BACKGROUND ART

A process for urea production typically includes a synthesis step, a high-pressure decomposition step, and a condensation step. In the synthesis step, urea is generated from ammonia ($NH_3$) and carbon dioxide ($CO_2$). Specifically, as shown by Formula (1), ammonium carbamate ($NH_2COONH_4$) is generated by the reaction of ammonia ($NH_3$) and carbon dioxide ($CO_2$). Furthermore, as shown by Formula (2), urea ($NH_2CONH_2$) and water ($H_2O$) are generated by a dehydration reaction of ammonium carbamate.

$$2NH_3 + CO_2 \rightarrow NH_2COONH_4 \quad (1)$$

$$NH_2COONH_4 \rightarrow NH_2CONH_2 + H_2O \quad (2)$$

The both reactions are equilibrium reactions and the reaction of Formula (2) is rate-determining as it is slower than the reaction of Formula (1).

In the high-pressure decomposition step, the urea synthesis solution obtained in the synthesis step is heated to decompose the ammonium carbamate contained in the urea synthesis solution into ammonia and carbon dioxide. Thereby, a gaseous mixture containing ammonia and carbon dioxide, and a urea synthesis solution having a higher urea concentration are obtained. In the condensation step, the gaseous mixture obtained in the high-pressure decomposition step is condensed. In the high-pressure decomposition step, medium-pressure steam is used as a heat source.

Regarding such a process for urea production, Patent Literature 1 discloses that, in a heat exchanger, raw material ammonia is heated to 175° C. by steam condensate. Patent Literatures 2 and 3 disclose methods in which medium-pressure steam condensate generated from medium-pressure steam, which has been used for heating in a high-pressure decomposition step, is used as a heat source in a medium-pressure decomposition step. In the medium-pressure decomposition step, ammonium carbamate contained in a urea synthesis solution obtained in the high-pressure decomposition step is decomposed at a pressure lower than the pressure in the high-pressure decomposition step.

Patent Literature 4 discloses that, in a stripper used in a high-pressure decomposition step, medium-pressure steam is used to heat an upper section of the stripper, and steam obtained by pressurizing low-pressure steam by an ejector with medium-pressure steam as a driving fluid is used to heat a lower section of the stripper.

CITATION LIST

Patent Literature

Patent Literature 1: JP H10-182587A
Patent Literature 2: GB 1542371A
Patent Literature 3: WO 03/064379 A1
Patent Literature 4: JP S61-10547A

SUMMARY OF INVENTION

Technical Problem

It is understood from Patent Literature 1 that the steam condensate used to heat the raw material ammonia is medium-pressure steam condensate generated from the medium-pressure steam in the high-pressure decomposition step. Therefore, this document suggests a method in which medium-pressure steam condensate is used to preheat raw material ammonia. As described before, Patent Literatures 2 and 3 disclose methods in which medium-pressure steam condensate is used as a heat source in a medium-pressure decomposition step.

However, in the case of using steam condensate to heat another fluid, the overall heat transfer coefficient tends to be low in comparison with the case of using steam. Further, since the pressure of the medium-pressure steam condensate is high, a design pressure for equipment and piping for heating said another fluid by the medium-pressure steam condensate becomes high.

An object of the present invention is to provide a process and an apparatus for urea production in which preheating of raw material ammonia or heating in a medium-pressure decomposition step can be performed at a relatively low pressure while decrease in an overall heat transfer coefficient is prevented.

Solution to Problem

An aspect of the present invention provides a process for urea production, including:

a synthesis step of synthesizing urea from ammonia and carbon dioxide to generate a urea synthesis solution;

a high-pressure decomposition step of, by heating the urea synthesis solution generated in the synthesis step with use of medium-pressure steam as a heat source, decomposing ammonium carbamate, separating a gaseous mixture containing ammonia and carbon dioxide from the urea synthesis solution and obtaining medium-pressure steam condensate;

a condensation step of absorbing and condensing at least a part of the gaseous mixture obtained in the high-pressure decomposition step in an absorption medium, and generating low-pressure steam with use of heat generated during the condensation;

a first medium-low-pressure steam generation step of, by reducing a pressure of the medium-pressure steam condensate obtained in the high-pressure decomposition step to a medium-low pressure lower than a pressure of the medium-pressure steam and higher than a pressure of the low-pressure steam, generating medium-low-pressure steam and medium-low-pressure steam condensate; and one or both of a medium-pressure decomposition step and an ammonia preheating step, wherein in the medium-pressure decomposition step, by heating the urea synthesis solution, said urea synthesis solution having been processed in the high-pressure decomposition step, at a pressure lower than a pressure in the high-pressure decomposition step with use of at least a part of the medium-low-pressure steam generated in the first medium-low-pressure steam generation step as a heat source, ammonium carbamate is decomposed, and a gaseous mixture containing ammonia and carbon dioxide is separated from the urea synthesis solution; and in the ammonia preheating step, the ammonia to be supplied to the synthesis step is heated with use of at least a part of the medium-low-pressure steam generated in the first medium-low-pressure steam generation step as a heat source.

Another aspect of the present invention provides an apparatus for urea production, including:

a synthesis reactor configured to synthesize urea from ammonia and carbon dioxide to generate a urea synthesis solution;

a high-pressure decomposer configured to, by heating the urea synthesis solution generated by the synthesis reactor with use of medium-pressure steam as a heat source, decompose ammonium carbamate, separate a gaseous mixture containing ammonia and carbon dioxide from the urea synthesis solution and obtain medium-pressure steam condensate;

a condenser configured to absorb and condense at least a part of the gaseous mixture obtained by the high-pressure decomposer in an absorption medium, and generate low-pressure steam with use of heat generated during the condensation;

a first medium-low-pressure steam generator configured to, by reducing a pressure of the medium-pressure steam condensate obtained by the high-pressure decomposer to a medium-low pressure lower than a pressure of the medium-pressure steam and higher than a pressure of the low-pressure steam, generate medium-low-pressure steam and medium-low-pressure steam condensate; and one or both of a medium-pressure decomposer and an ammonia preheater, wherein the medium-pressure decomposer is configured to, by heating the urea synthesis solution, said urea synthesis solution having been processed by the high-pressure decomposer, at a pressure lower than a pressure in the high-pressure decomposer with use of at least a part of the medium-low-pressure steam generated by the first medium-low-pressure steam generator as a heat source, decompose ammonium carbamate, and separate a gaseous mixture containing ammonia and carbon dioxide from the urea synthesis solution; and the ammonia preheater is configured to heat the ammonia to be supplied to the synthesis reactor, with use of at least a part of the medium-low-pressure steam generated by the first medium-low-pressure steam generator as a heat source.

Advantageous Effects of Invention

The present invention provides a process and an apparatus for urea production in which preheating of raw material ammonia or heating in a medium-pressure decomposition step can be performed at a relatively low pressure while decrease in an overall heat transfer coefficient is prevented.

DESCRIPTION OF EMBODIMENTS

Figure 1:
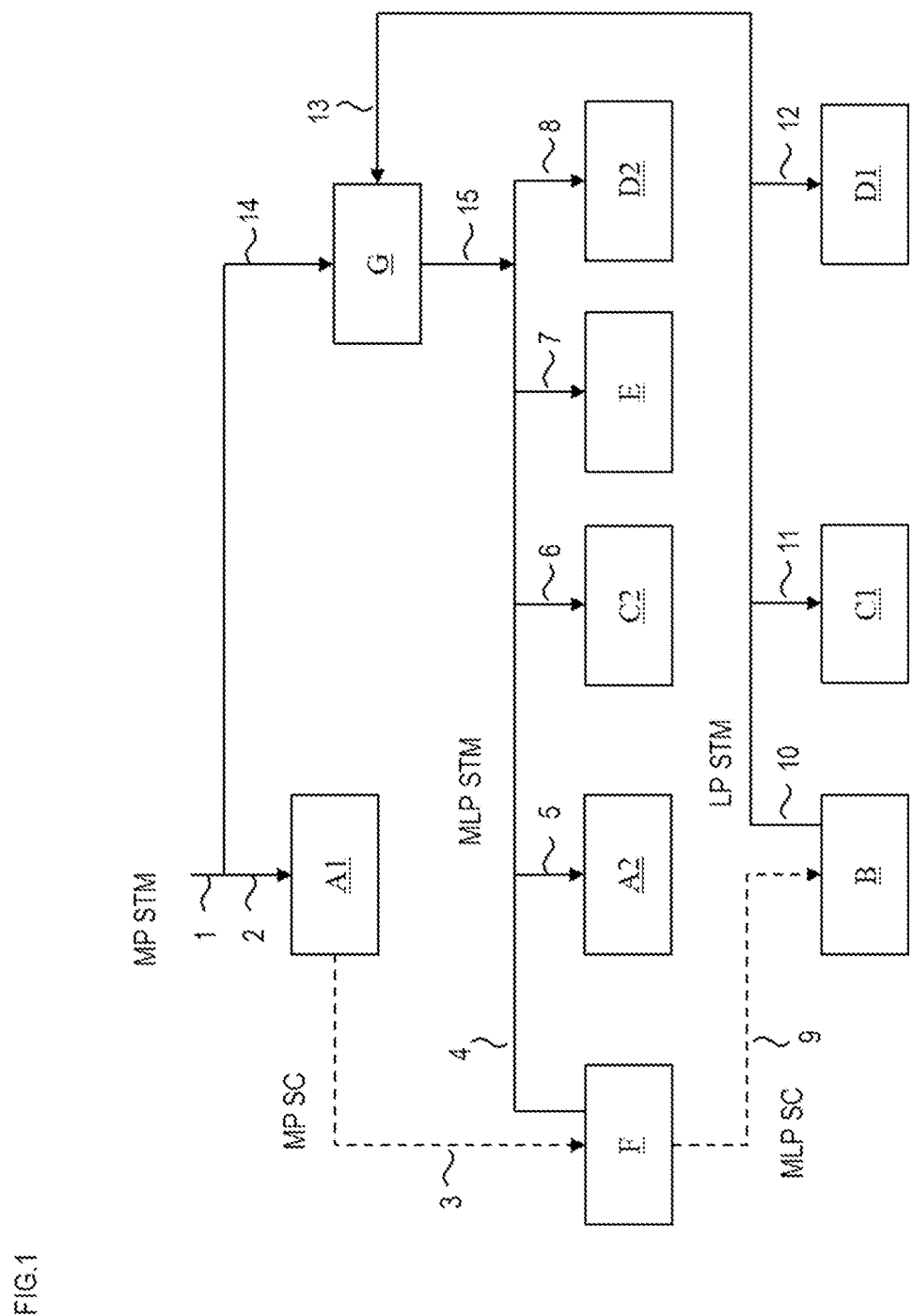
FIG. 1 is a schematic diagram for illustrating an example of production and use of medium-low-pressure steam.

A process for urea production according to the present invention includes a synthesis step, a high-pressure decomposition step, a condensation step and a first medium-low-pressure steam generation step. The process for urea production also includes one or both of a medium-pressure decomposition step and an ammonia preheating step, and includes the medium-pressure decomposition step in particular.

[Synthesis Step]

In the synthesis step, urea is synthesized from ammonia and carbon dioxide to generate a urea synthesis solution. In the synthesis step, urea is also synthesized from ammonium carbamate contained in a recycled liquid from a condensation step that will be described later.

An operating pressure in the synthesis step is typically 130 bars (absolute pressure, which also applies to the following description) to 250 bars, preferably 140 bars to 200 bars. The operating temperature of the synthesis step is typically 160° C. to 200° C., preferably 170° C. to 190° C.

[High-Pressure Decomposition Step]

In the high-pressure decomposition step, the urea synthesis solution generated in the synthesis step is heated with use of medium-pressure steam as a heat source. Thereby, ammonium carbamate contained in the urea synthesis solution obtained in the synthesis step is decomposed, and a gaseous mixture containing ammonia and carbon dioxide is separated from the urea synthesis solution. The gaseous mixture obtained in the high-pressure decomposition step may be hereinafter referred to as "high-pressure decomposition outlet gas". By condensation of the medium-pressure steam used as a heat source, medium-pressure steam condensate is generated.

Heating in the high-pressure decomposition step requires a high-temperature heating medium. Low-pressure steam recovered in the condensation step, which will be described later, does not have a sufficiently high temperature for the heating. Therefore, medium-pressure steam having a pressure higher than the pressure of the low-pressure steam is used in the heating.

The pressure of the medium-pressure steam is typically 12 bars to 40 bars, preferably 14 bars to 25 bars. The medium-pressure steam is often appropriately generated as back-pressure steam of a steam turbine in a plant for urea production. Alternatively, the medium-pressure steam can be supplied from the outside of the plant for urea production.

The operating temperature of the high-pressure decomposition step is typically 150° C. to 220° C., preferably 160° C. to 200° C.

Specifically, the urea synthesis solution obtained in the synthesis step is mainly composed of urea, unreacted ammonia, unreacted carbon dioxide, unreacted ammonium carbamate and water. The urea synthesis solution is usually heated under a pressure substantially equal to the pressure in the synthesis step. As a consequence, the unreacted ammonia, the unreacted carbon dioxide, the unreacted ammonium carbamate and water are separated as a gaseous mixture mainly composed of ammonia, carbon dioxide and water (steam).

In the high-pressure decomposition step, it is possible to use a decomposition method in which only heating is performed. However, in order to promote decomposition, it is possible to use a stripping process in which, in addition to heating, carbon dioxide gas is supplied and brought into contact with a urea synthesis solution.

[Condensation Step]

In the condensation step, at least a part of the gaseous mixture (high-pressure decomposition outlet gas) obtained in the high-pressure decomposition step is absorbed and condensed in an absorption medium. With use of heat generated during the condensation, low-pressure steam is generated. The gaseous mixture and the absorption medium in the condensation step may be referred as an "internal fluid" of a condenser.

The pressure of the low-pressure steam is typically 3 bars to 9 bars, more preferably 5 bars to 7 bars. The low-pressure steam can be obtained by vaporizing appropriate water, for example, low-pressure steam condensate.

As the absorption medium, an absorption medium publicly known in the field of the process for urea production, such as water (which may contain urea, ammonia, carbon dioxide, and ammonium carbamate), can be appropriately used.

The temperature of a liquid (process fluid) obtained in the condensation step is typically 100° C. to 210° C., preferably 160° C. to 190° C. Since the high-pressure process (including the synthesis step, the high-pressure decomposition step and the condensation step) in urea production has nothing that results in pressure reduction except pressure loss, the synthesis step, the high-pressure decomposition step and the condensation step are operated at substantially the same pressure. It should be noted that pressurization by an ejector is performed for recycling which will be described later.

Specifically, the gaseous mixture (the high-pressure decomposition outlet gas) separated in the high-pressure decomposition step is introduced into the condensation step, where the gaseous mixture comes into contact with the absorption medium containing water under cooling, and the gaseous mixture condenses. During the condensation, a part of ammonia and a part of carbon dioxide turn into ammonium carbamate (see Formula (1)), and, the urea synthesis reaction (see Formula (2)) also progresses by keeping the condensation temperature high.

When the gaseous mixture condenses in the condensation step, a large amount of heat is generated at a high temperature. To effectively use the generated heat, heat recovery is performed. As a method for the heat recovery, there is a method in which heat is exchanged between the urea synthesis solution that has been processed in the high-pressure decomposition step (a liquid containing unreacted ammonia, unreacted carbon dioxide, unreacted ammonium carbamate and water that have not been separated) and an internal fluid of a condenser. Alternatively, there is a method of performing heat exchange between an internal fluid of a condenser and hot water (pressurized water is often used) to obtain the hot water whose temperature has been increased. In many cases, however, a method of performing heat exchange between an internal fluid of a condenser and steam condensate (in particular, low-pressure steam condensate) to generate low-pressure steam is used. This method may be used in combination with at least one of the two methods described above.

For the heat exchange between the internal fluid of the condenser and the steam condensate, a vertical or horizontal shell & tube heat exchanger may be used. Though the gaseous mixture may be condensed on the tube side, the gaseous mixture may be condensed on the shell side so that residence time in the condensation step can be long for the sake of condensation and reaction.

Gas that has not condensed in the condensation step can be recovered as a recovered liquid, when the gas is absorbed and condensed in an absorption medium and the absorption medium is simultaneously cooled. By returning the recovered liquid to the high-pressure process (including the synthesis step, the high-pressure decomposition step and the condensation step), typically to the condensation step, unreacted ammonia and unreacted carbon dioxide can be recovered. As the absorption medium, an absorption medium publicly known in the field of the process for urea production, such as water (which may contain urea, ammonia, carbon dioxide and ammonium carbamate) can be appropriately used.

[Recycling]

A structure may be used in which a condensed liquid obtained in the condensation step is sent to the synthesis step again so that unreacted ammonia and unreacted carbon dioxide are recycled. As a method for recycling the condensed liquid obtained in the condensation step, there is a method in which a synthesis reactor (for performing the synthesis step) is arranged below, and a condenser (for performing the condensation step) is arranged above the synthesis reactor so as to recycle the condensed liquid using gravity. As another recycling method, there is a method in which, with use of ammonia to be supplied to a synthesis reactor as a driving fluid, a condensed liquid obtained in the condensation step is pressurized by an ejector to recycle the condensed liquid. The recycling method using gravity and the recycling method using an ejector may be used in combination.

[First Medium-Low-Pressure Steam Generation Step]

In the first medium-pressure steam generation step, the pressure of the medium-pressure steam condensate obtained in the high-pressure decomposition step is reduced to a medium-low pressure to generate medium-low-pressure steam and medium-low-pressure steam condensate. The medium-low pressure means a pressure lower than the pressure of medium-pressure steam but is higher than the pressure of low-pressure steam. A pressure reducing valve may be appropriately used for the pressure reduction, and a gas-liquid separator may be used to separate the generated medium-low-pressure steam and medium-low-pressure steam condensate.

The pressure of the medium-low-pressure steam is, for example, 7 bars to 18 bars, preferably 8 bars to 12 bars.

[Medium-Pressure Decomposition Step]

In the medium-pressure decomposition step, with use of at least a part of the medium-low-pressure steam generated in the first medium-low-pressure steam generation step as a heat source, the urea synthesis solution that has been processed in the high-pressure decomposition step is heated at a pressure lower than a pressure in the high-pressure decomposition step. Thereby, the ammonium carbamate contained in the urea synthesis solution that has been processed in the high-pressure decomposition step is decomposed. In the medium-pressure decomposition step, a gaseous mixture containing ammonia and carbon dioxide (this gaseous mixture may be hereinafter referred to as "medium-pressure decomposition outlet gas") and a urea synthesis solution having a further reduced concentration of ammonium carbamate are obtained.

Specifically, the urea synthesis solution that has been processed in the high-pressure decomposition step (the liquid containing unreacted ammonia, unreacted carbon dioxide, unreacted ammonium carbamate and water that have not been separated) is subjected to processing by pressure reduction and heating. Thereby, the unreacted ammonia, the unreacted carbon dioxide, the unreacted ammonium carbamate and the water are separated as a gaseous mixture mainly composed of ammonia, carbon dioxide and water (steam).

The medium-pressure decomposition outlet gas can be recovered as a recovered liquid, when the gas is absorbed and condensed in an absorption medium and the absorption medium is simultaneously cooled. In this context, if the processing by the pressure reduction and the heating are performed at a plurality of stages as described later, the above-mentioned "medium-pressure decomposition outlet gas" means a gaseous mixture containing ammonia and carbon dioxide that is obtained at each stage. By returning the recovered liquid to the high-pressure process, typically to the condensation step, unreacted ammonia and unreacted carbon dioxide can be recovered. As the absorption medium, an absorption medium publicly known in the field of the process for urea production, such as water (which may contain urea, ammonia, carbon dioxide, and ammonium carbamate) can be appropriately used.

By reducing as far as possible the pressure of the urea synthesis solution that has been processed in the high-pressure decomposition step, the unreacted ammonia, unreacted carbon dioxide, unreacted ammonium carbamate and water that have not been separated can be more easily separated as a gaseous mixture. On the other hand, in order to cause the gaseous mixture to be absorbed into an absorption medium under cooling, recovered as a recovered liquid and returned to the condensation step whose operating pressure is high, it is advantageous that the pressure of the urea synthesis solution is as high as possible. Therefore, it is preferable to divide the processing by the pressure reduction and the heating into a plurality of stages, and to subject the urea synthesis solution that has been processed in the high-pressure decomposition step to said plurality of stages. Thereby it is possible to effectively reduce the content of unreacted ammonia, unreacted carbon dioxide, unreacted ammonium carbamate and water, and to obtain high-purity product urea. It is preferable to heat the urea synthesis solution that has been processed in the medium-pressure decomposition step at a pressure lower than a pressure in the medium-pressure decomposition step (however, equal to or higher than the atmospheric pressure) after the medium-pressure decomposition step.

In the medium-pressure decomposition step, the urea synthesis solution (containing unreacted ammonia, unreacted carbon dioxide, unreacted ammonium carbamate and water that have not been separated) is heated, directly after the urea synthesis solution has been processed in the high-pressure decomposition step, at a pressure lower than the pressure in the high-pressure decomposition step so as to obtain the gaseous mixture (the medium-pressure decomposition outlet gas). However, as described before, there may be a case where heat recovery is performed in the condensation step by heat exchange between the internal fluid of the condenser and the urea synthesis solution directly after the urea synthesis solution has been processed in the high-pressure decomposition step. In this case, the medium-pressure decomposition step means a step of heating the urea synthesis solution that has been heated by this heat recovery, at a pressure lower than the pressure in the high-pressure decomposition step to separate the gaseous mixture.

The operating pressure in the medium-pressure decomposition step depends on the number of the stages of the processing by the pressure reduction and the heating. For example, in the case of two stages (the medium-pressure decomposition step and the low-pressure decomposition step), the operating pressure is typically 3 bars to 130 bars, preferably 6 bars to 70 bars, and more preferably 10 bars to 20 bars. The operating temperature of the medium-pressure decomposition step depends on the operating pressure but is typically 100° C. to 180° C., preferably on the order of 130° C. to 160° C.

The urea synthesis solution obtained in the medium-pressure decomposition step can be sent to a concentration step. In this context, if the processing by the pressure reduction and the heating are performed at a plurality of stages, the above-mentioned "urea synthesis solution obtained in the medium-pressure decomposition step" means the urea synthesis solution obtained at the last stage. In the concentration step, the content of water contained in the urea synthesis solution is reduced by heating under vacuum. Urea obtained in the concentration step may be product urea. Alternatively, a granulation step may be performed after the concentration step to obtain granular product urea.

A medium-pressure decomposer for performing the medium-pressure decomposition step may have a structure for heat exchange between the medium-low-pressure steam and the process fluid (urea synthesis solution). A pressure reducing valve for performing the pressure reduction may be arranged upstream from the medium-pressure decomposer in relation to the flow direction of the process fluid (urea synthesis solution).

[Ammonia Preheating Step]

In the ammonia preheating step, with use of at least a part of the medium-low-pressure steam generated in the first medium-low-pressure steam generation step as a heat source, ammonia to be supplied to the synthesis step is heated. The higher the temperature in the synthesis step is, the higher the equilibrium synthesis rate from ammonium carbamate to urea is, and the higher the conversion speed is, and further, the higher the conversion rate is if the residence time is the same. As a result, the amount of steam required to decompose unreacted ammonium carbamate is reduced. As a method for increasing the temperature in the synthesis step, a method of increasing the temperature of raw material ammonia to be supplied to the synthesis step is effective.

An appropriate heat exchanger may be used in the ammonia preheating step for performing heat exchange between ammonia and medium-low-pressure steam.

[Second Medium-Pressure Steam Generation Step]

By pressurizing low-pressure steam by an ejector using medium-pressure steam as a driving fluid, it is possible to perform the second medium-low-pressure steam generation step of generating medium-low-pressure steam having a pressure lower than the pressure of the medium-pressure steam and higher than the pressure of the low-pressure steam. An ejector is used to perform this step. In this step, the medium-low-pressure steam may be generated by pressurizing low-pressure steam by an ejector using high-pressure steam having a pressure higher than the medium-pressure steam as a driving fluid. The ejector for which the medium-pressure steam is used as a driving fluid and the ejector for which the high-pressure steam is used as a driving fluid may be used together. The high-pressure steam is, for example, steam to be supplied to a steam turbine. By this step, it is possible to increase heat sources having a temperature higher than the temperature of the low-pressure steam while effectively utilizing the low-pressure steam.

In one or both of the medium-pressure decomposition step and the ammonia preheating step, at least a part of the medium-low-pressure steam generated in the second medium-low-pressure steam generation step may be used as a heat source.

The medium-low-pressure steam obtained in the second medium-low-pressure steam generation step may have a pressure similar to or the same as the pressure of the medium-low-pressure steam obtained in the first medium-low-pressure steam generation step. The medium-low-pressure steam obtained in the second medium-low-pressure steam generation step may be appropriately mixed with the medium-low-pressure steam obtained in the first medium-low-pressure steam generation step.
[Heating by Medium-Low-Pressure Steam in High-Pressure Decomposition Step]

In the high-pressure decomposition step, it is possible to, after heating the urea synthesis solution generated in the synthesis step with use of medium-pressure steam as a heat source, heat the urea synthesis solution with use of medium-low-pressure steam as a heat source. As the medium-low-pressure steam used for this purpose, at least a part of the medium-low-pressure steam generated in the first medium-low-pressure steam generation step may be used. As the medium-low-pressure steam used for this purpose, at least a part of the medium-low-pressure steam generated in the second medium-low-pressure steam generation step may be used.

For example, a heating part of a high-pressure decomposer (typically, a stripper) may be divided into an upstream section and a downstream section in relation to the flow direction of the process fluid (urea synthesis solution), and the medium-pressure steam and the medium-low-pressure steam may be used to heat the upstream section and the downstream section, respectively. Thereby, it is possible to effectively use medium-low-pressure steam and reduce the overall amount of consumption of medium-pressure steam, hydrolysis of urea and generation of biuret.

[Use of Medium-Low-Pressure Steam Condensate]

When medium-low-pressure steam is consumed as a heat source, the medium-low-pressure steam condenses to generate medium-low-pressure steam condensate. Further, as described before, medium-low-pressure steam condensate is generated in the first medium-low-pressure steam generation step. The medium-low-pressure steam condensate may be used as a heat source in one or both of the medium-pressure decomposition step and the ammonia preheating step. As the medium-low-pressure steam condensate used for this purpose, there may be used at least a part of the medium-low-pressure steam condensate formed by condensation of the medium-low-pressure steam generated in the first medium-low-pressure steam generation step. Further, as the medium-low-pressure steam condensate used for this purpose, there may be used at least a part of the medium-low-pressure steam condensate generated in the first medium-low-pressure steam generation step. As the medium-low-pressure steam condensate used for this purpose, there may be used at least a part of the medium-low-pressure steam condensate formed by condensation of the medium-low-pressure steam generated in the second medium-low-pressure steam generation step.

Thus, medium-low-pressure steam condensate may be effectively used as a heat source in the medium-pressure decomposition step or/and the ammonia preheating step. Therefore, the medium-pressure decomposer may have a structure for heat exchange between a process fluid and medium-low-pressure steam condensate. Further, an appropriate heat exchanger that performs heat exchange between raw material ammonia and medium-low-pressure steam condensate may be used. Alternatively, the pressure of medium-low-pressure steam condensate may be reduced to a low pressure to generate low-pressure steam.

In the case of heating a fluid such as raw material ammonia or a process fluid in the medium-pressure decomposition step, for example, heating by low-pressure steam, heating by medium-low-pressure steam condensate and heating by medium-low-pressure steam may be performed in this order.

[Others]

Since the urea synthesis reaction also progresses in the condensation step, the condensation step and the synthesis step may be carried out in a single pressure vessel. Therefore, it is possible to use a single pressure vessel in which a condenser and a synthesis reactor are integrated.

Prior to preheating of raw material ammonia by medium-low-pressure steam, the raw material ammonia may be preheated by low-pressure steam.

According to the present invention, since steam is used as a heat source, the overall heat transfer coefficient becomes higher in comparison with the case of using steam condensate. Further, since the pressure of medium-low-pressure steam is lower in comparison with medium-pressure steam condensate, the design pressure for equipment and piping can be set lower, and equipment cost can be reduced. Furthermore, in comparison with medium-pressure steam condensate, medium-low-pressure steam is easy to distribute for heating to a plurality of steps, such as the medium-pressure decomposition step, the ammonia preheating step and the high-pressure decomposition step. In other words, regarding heat distribution, flexibility in design and operation is high.

[Process Example]

The present invention will be described below in detail with reference to drawings, but the present invention is not limited thereto.

FIG. 1 schematically shows an embodiment of production and use of medium-low-pressure steam in an example of a urea production process. In the drawings, "MP STM" means medium-pressure steam; "MLP STM" means medium-low-pressure steam; "LP STM" means low-pressure steam; "MP SC" means medium-pressure steam condensate; "MLP SC" means medium-low-pressure steam condensate; and "LP SC (shown in FIG. 2)" means low-pressure steam condensate, respectively.

Medium-pressure steam is supplied via lines 1 and 2 to heating section A1, which performs heating by using medium-pressure steam, of the high-pressure decomposer. This medium-pressure steam is used as a heat source in heating section A1, and condenses to become medium-pressure steam condensate (line 3). This medium-pressure steam condensate is supplied to first medium-low-pressure steam generator F. First medium-low-pressure steam generator F is typically provided with a pressure reducing valve and, furthermore, may be provided with a gas-liquid separator (vessel). In first medium-low-pressure steam generator F, the medium-pressure steam condensate is reduced in pressure, and medium-low-pressure steam is generated. At this time, a liquid phase (medium-low-pressure steam condensate) may be generated. In the embodiment shown in FIG. 1, the medium-low-pressure steam is withdrawn from line 4, and the medium-low-pressure steam condensate is withdrawn from line 9.

The medium-low-pressure steam is supplied to heating section A2, which performs heating by using medium-low-pressure steam, of the high-pressure decomposer, to heating section C2, which performs heating by using medium-low-pressure steam, of the medium-pressure decomposer, to ammonia preheater E which performs heating by using medium-low-pressure steam and to other equipment D2 that consumes medium-low-pressure steam via lines 5, 6, 7 and 8, respectively, and used as heat sources.

The medium-low-pressure steam condensate of line 9 is reduced in pressure, for example, by a pressure reducing valve, and low-pressure steam and low-pressure steam condensate are generated. These are separated by a gas-liquid separator. This low-pressure steam condensate is heated by condenser B (in other words, used to recover heat of condensation) and becomes low-pressure steam. The pressure reducing valve and the gas-liquid separator are not shown in FIG. 1. It should be understood that, in FIG. 1, the pressure reducing valve and the gas-liquid separator are included in the block indicating condenser B.

The low-pressure steam is withdrawn from condenser B via line 10, supplied to heating section C1, which performs heating by using low-pressure steam, of the medium-pressure decomposer and other equipment D1 that consumes low-pressure steam via lines 11 and 12, respectively, and used as heat sources. The low-pressure steam from line 10 is also supplied via line 13 to second medium-low-pressure steam generator (ejector) G.

Ejector G is driven by medium-pressure steam from line 14, and the low-pressure steam (line 13) is pressurized to generate medium-low-pressure steam (line 15). The medium-low-pressure steam from line 15 is mixed with the medium-low-pressure steam from line 4.

Figure 2:
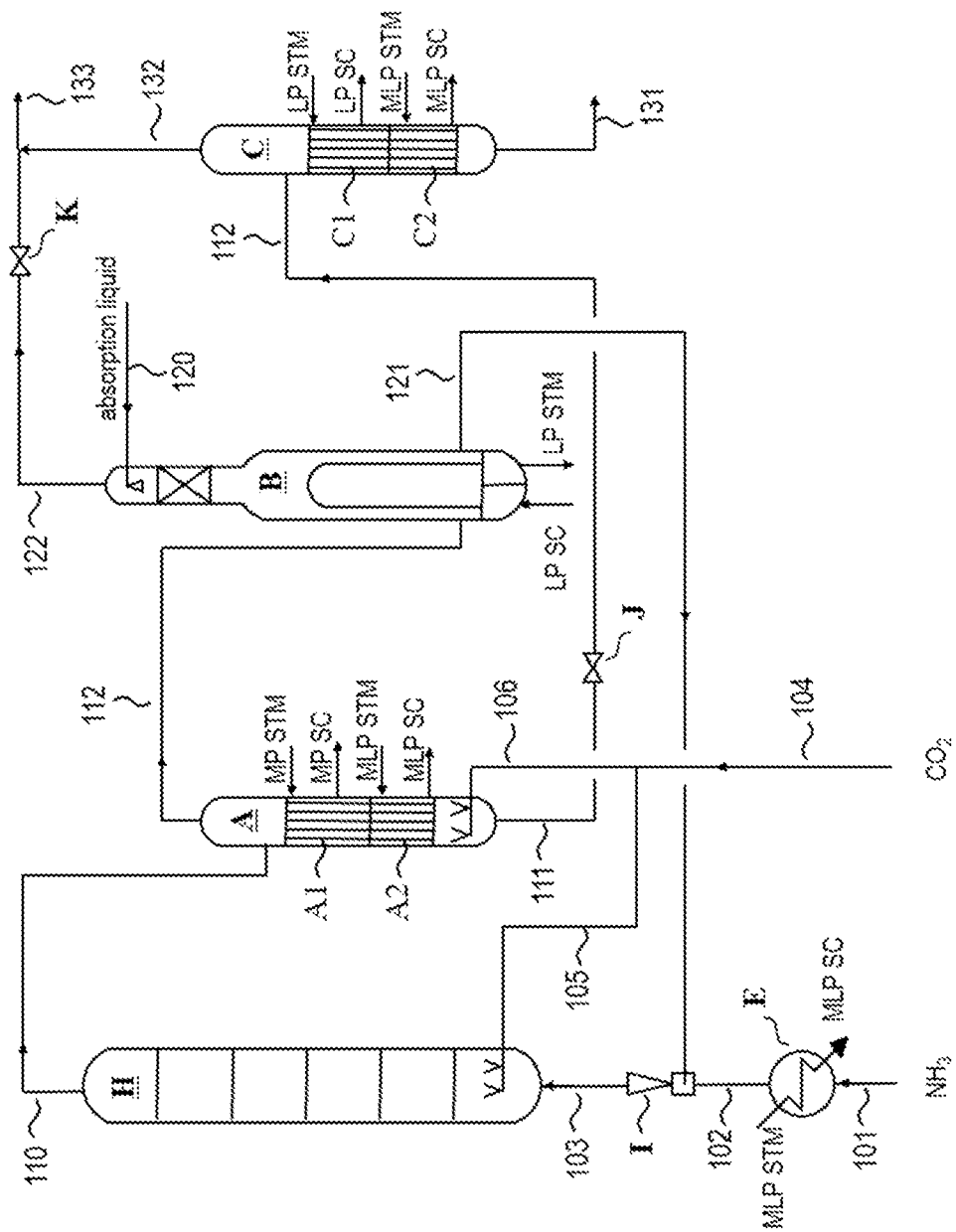
FIG. 2 is a process flow diagram schematically showing an example of a plant for urea production.

FIG. 2 is a process flow diagram schematically showing an example of a urea production process. Raw material ammonia appropriately pressurized by a pump (not shown) is supplied to synthesis reactor H via lines 101, 102 and 103. Raw material carbon dioxide is supplied to synthesis reactor H via lines 104 and 105. Raw material ammonia can be heated by heat exchange with medium-low-pressure steam in ammonia preheater E and, after that, can be used as a driving fluid for ejector I. A urea synthesis solution is sent from synthesis reactor H to high-pressure decomposer A via line 110.

In high-pressure decomposer A, the urea synthesis solution is heated in heating section A1 which performs heating by using medium-pressure steam, and then heated in heating section A2 which performs heating by using medium-low-pressure steam. High-pressure decomposer A has a structure (heating section A1) for heat exchange between medium-pressure steam and the process fluid on the upstream side and a structure (heating section A2) for heat exchange between medium-low-pressure steam and the process fluid on the downstream side in relation to the flow direction of the process fluid (urea synthesis solution). Carbon dioxide is supplied to the bottom of high-pressure decomposer A as a stripping gas from line 106.

High-pressure decomposition outlet gas is supplied to condenser B from high-pressure decomposer A via line 112. Further, the urea synthesis solution from which the high-pressure decomposition outlet gas has been separated is reduced in pressure by pressure reducing valve J after flowing through line 111, and supplied to medium-pressure decomposer C via 112.

The high-pressure decomposition outlet gas supplied to condenser B is absorbed by an absorption liquid (absorption medium) supplied from line 120, and condenses. The obtained condensed liquid is pressurized by ejector I after flowing through line 121, and recycled to synthesis reactor H from line 103. Gas which has not condensed (condenser outlet gas) is withdrawn from line 122 and reduced in pressure by pressure reducing valve K. Low-pressure steam condensate is supplied to condenser B as a cooling source. The low-pressure steam condensate is heated by the internal fluid (process fluid) of condenser B to generate low-pressure steam.

The urea synthesis solution (which may be a gas-liquid two-phase flow) supplied from line 112 to medium-pressure decomposer C is heated in heating section C1 which performs heating by using low-pressure steam, and then heated in heating section C2 which performs heating by using medium-low-pressure steam. Medium-pressure decomposer C has a structure (heating section C1) for heat exchange between low-pressure steam and the process fluid on the upstream side and a structure (heating section C2) for heat exchange between medium-low-pressure steam and the process fluid on the downstream side in relation to the flow direction of the process fluid (urea synthesis solution).

Medium-pressure decomposition outlet gas is withdrawn from line 132, and the urea synthesis solution from which the medium-pressure decomposition outlet gas has been separated is withdrawn from line 131.

The medium-pressure decomposition outlet gas (line 132) can be mixed with the condenser outlet gas which has been reduced in pressure by pressure reducing valve K (line 122) to obtain a gaseous mixture (line 133). This gaseous mixture can be recovered as a recovered liquid, when the gaseous mixture is absorbed and condensed in an absorption medium and the absorption medium is simultaneously cooled (not shown). As the absorption medium, an absorption medium publicly known in the field of the process for urea production, such as water (which may contain urea, ammonia, carbon dioxide, and ammonium carbamate), can be appropriately used.

The recovered liquid recovered in this way can be appropriately pressurized and used as an absorption medium in the condensation step. Further, the urea synthesis solution from which the medium-pressure decomposition gas has been separated (line 131) can be sent to the concentration step (not shown). It is possible to obtain product urea from the concentration step or obtain granular product urea via a granulation step after the concentration step.

REFERENCE SIGNS LIST

MP STM: medium-pressure steam
MLP STM: medium-low-pressure steam
LP STM: low-pressure steam
MP SC: medium-pressure steam condensate
MLP SC: medium-low-pressure steam condensate
LP SC: low-pressure steam condensate
A: high-pressure decomposer
A1: heating section, which performs heating by using medium-pressure steam, of the high-pressure decomposer
A2: heating section, which performs heating by using medium-low-pressure steam, of the high-pressure decomposer
B: condenser
C: medium-pressure decomposer
C1: heating section, which performs heating by using low-pressure steam, of the medium-pressure decomposer
C2: heating section, which performs heating by using medium-low-pressure steam, of the medium-pressure decomposer
D1: other equipment that consumes low-pressure steam
D2: other equipment that consumes medium-low-pressure steam
E: ammonia preheater which performs heating by using medium-low-pressure steam
F: first medium-low-pressure steam generator (reducing the pressure of medium-pressure steam condensate)
G: second medium-low-pressure steam generator (ejector)
H: synthesis reactor
I: ejector for recycling

The invention claimed is:

1. A process for urea production, comprising:
a synthesis step of synthesizing urea from ammonia and carbon dioxide to generate a urea synthesis solution;

a high-pressure decomposition step of, by heating the urea synthesis solution generated in the synthesis step with use of medium-pressure steam as a heat source, decomposing ammonium carbamate, separating a gaseous mixture containing ammonia and carbon dioxide from the urea synthesis solution and obtaining a medium-pressure steam condensate, wherein the medium-pressure steam has a pressure in a range from 12 bars to 40 bars;

a condensation step of absorbing and condensing at least a part of the gaseous mixture obtained in the high-pressure decomposition step in an absorption medium, and generating low-pressure steam with use of heat generated during the condensation;

a first medium-low-pressure steam generation step of, by reducing a pressure of the medium-pressure steam condensate obtained in the high-pressure decomposition step to a medium-low pressure lower than a pressure of the medium-pressure steam and higher than a pressure of the low-pressure steam, generating medium-low-pressure steam and a medium-low-pressure steam condensate; and one or both of a medium-pressure decomposition step and an ammonia preheating step, wherein in the medium-pressure decomposition step, by heating the urea synthesis solution, said urea synthesis solution having been processed in the high-pressure decomposition step, at a pressure lower than a pressure in the high-pressure decomposition step with use of at least a part of the medium-low-pressure steam generated in the first medium-low-pressure steam generation step as a heat source, ammonium carbamate is decomposed, and a gaseous mixture containing ammonia and carbon dioxide is separated from the urea synthesis solution, wherein an operating pressure in the medium-pressure decomposition step is in a range from 3 bars to 130 bars; and in the ammonia preheating step, the ammonia to be supplied to the synthesis step is heated with use of at least a part of the medium-low-pressure steam generated in the first medium-low-pressure steam generation step as a heat source.

2. The process for urea production according to claim 1, wherein, in the high-pressure decomposition step, following heating the urea synthesis solution generated in the synthesis step with use of the medium-pressure steam as a heat source, the urea synthesis solution is heated with use of at least a part of the medium-low-pressure steam generated in the first medium-low-pressure steam generation step as a heat source.

3. The process for urea production according to claim 1, wherein, in one or both of the medium-pressure decomposition step and the ammonia preheating step, at least a part of one or both of the medium-low-pressure steam condensate generated in the first medium-low-pressure steam generation step and a medium-low-pressure steam condensate formed by condensation of the medium-low-pressure steam generated in the first medium-low-pressure steam generation step are used as a heat source.

4. The process for urea production according to claim 1, comprising a second medium-low-pressure steam generation step of generating medium-low-pressure steam having a pressure lower than the pressure of the medium-pressure steam and higher than the pressure of the low-pressure steam; wherein the second medium-low-pressure steam generation step comprises one or both of pressurizing the low-pressure steam by an ejector with use of the medium-pressure steam as a driving fluid and pressurizing the low-pressure steam by an ejector with use of high-pressure steam as a driving fluid.

5. The process for urea production according to claim 4, wherein, in one or both of the medium-pressure decomposition step and the ammonia preheating step, at least a part of the medium-low-pressure steam generated in the second medium-low-pressure steam generation step is used as a heat source.

6. The process for urea production according to claim 4, wherein, in the high-pressure decomposition step, following heating the urea synthesis solution generated in the synthesis step with use of the medium-pressure steam as a heat source, the urea synthesis solution is heated with use of at least a part of the medium-low-pressure steam generated in the second medium-low-pressure steam generation step as a heat source.

7. The process for urea production according to claim 4, wherein, in one or both of the medium-pressure decomposition step and the ammonia preheating step, at least a part of a medium-low-pressure steam condensate formed by condensation of the medium-low-pressure steam generated in the second medium-low-pressure steam generation step is used as a heat source.

8. The process for urea production according to claim 1, wherein the synthesis step and the condensation step are performed in a pressure vessel in which a condenser and a synthesis reactor are integrated.

9. The process for urea production according to claim 1, comprising the medium-pressure decomposition step.

10. An apparatus for urea production, comprising:

a synthesis reactor configured to synthesize urea from ammonia and carbon dioxide to generate a urea synthesis solution;

a high-pressure decomposer configured to, by heating the urea synthesis solution generated by the synthesis reactor with use of medium-pressure steam as a heat source, decompose ammonium carbamate, separate a gaseous mixture containing ammonia and carbon dioxide from the urea synthesis solution and obtain a medium-pressure steam condensate, wherein the medium-pressure steam has a pressure in a range from 12 bars to 40 bars;

a condenser configured to absorb and condense at least a part of the gaseous mixture obtained by the high-pressure decomposer in an absorption medium, and generate low-pressure steam with use of heat generated during the condensation;

a first medium-low-pressure steam generator configured to, by reducing a pressure of the medium-pressure steam condensate obtained by the high-pressure decomposer to a medium-low pressure lower than a pressure of the medium-pressure steam and higher than a pressure of the low-pressure steam, generate medium-low-pressure steam and a medium-low-pressure steam condensate; and one or both of a medium-pressure decomposer and an ammonia preheater, wherein the medium-pressure decomposer is configured to, by heating the urea synthesis solution, said urea synthesis solution having been processed by the high-pressure decomposer, at a pressure lower than a pressure in the high-pressure decomposer with use of at least a part of the medium-low-pressure steam generated by the first medium-low-pressure steam generator as a heat source, decompose ammonium carbamate, and separate a gaseous mixture containing ammonia and carbon dioxide from the urea synthesis solution, wherein an operating pressure in the medium-pressure decomposer is in a range from 3 bars to 130 bars; and the ammonia preheater is configured to heat the ammonia to be supplied to the synthesis reactor, with use of at least a part of the medium-low-pressure steam generated by the first medium-low-pressure steam generator as a heat source.

11. The apparatus for urea production according to claim 10, wherein the high-pressure decomposer is configured to, following heating the urea synthesis solution generated by the synthesis reactor with use of the medium-pressure steam as a heat source, heat the urea synthesis solution with use of at least a part of the medium-low-pressure steam generated by the first medium-low-pressure steam generator as a heat source.

12. The apparatus for urea production according to claim 10, wherein one or both of the medium-pressure decomposer and the ammonia preheater are configured to use, as a heat source, at least a part of one or both of the medium-low-pressure steam condensate generated by the first medium-low-pressure steam generator and a medium-low-pressure steam condensate formed by condensation of the medium-low-pressure steam generated by the first medium-low-pressure steam generator.

13. The apparatus for urea production according to claim 10, comprising a second medium-low-pressure steam generator configured to generate medium-low-pressure steam having a pressure lower than the pressure of the medium-pressure steam and higher than the pressure of the low-pressure steam; wherein the second medium-low-pressure steam generator comprises one or both of an ejector for pressurizing the low-pressure steam with use of the medium-pressure steam as a driving fluid and an ejector for pressurizing the low-pressure steam with use of high-pressure steam as a driving fluid.

14. The apparatus for urea production according to claim 13, wherein one or both of the medium-pressure decomposer and the ammonia preheater are configured to use at least a part of the medium-low-pressure steam generated by the second medium-low-pressure steam generator as a heat source.

15. The apparatus for urea production according to claim 13, wherein the high-pressure decomposer is configured to, following heating the urea synthesis solution generated by the synthesis reactor with use of the medium-pressure steam as a heat source, heat the urea synthesis solution with use of at least a part of the medium-low-pressure steam generated by the second medium-low-pressure steam generator as a heat source.

16. The apparatus for urea production according to claim 13, wherein one or both of the medium-pressure decomposer and the ammonia preheater are configured to use at least a part of a medium-low-pressure steam condensate formed by condensation of the medium-low-pressure steam generated by the second medium-low-pressure steam generator as a heat source.

17. The apparatus for urea production according to claim 10, wherein the synthesis reactor and the condenser are integrated in one pressure vessel.

18. The apparatus for urea production according to claim 10, comprising the medium-pressure decomposer.

* * * * *